(12) United States Patent
Claypool et al.

(10) Patent No.: US 9,668,826 B2
(45) Date of Patent: Jun. 6, 2017

(54) HANDHELD VISCOUS DENTAL PASTE DISPENSER

(71) Applicant: 3M INNOVATIVE PROPERTIES COMPANY, St. Paul, MN (US)

(72) Inventors: Christopher J. Claypool, Woodbury, MN (US); Bruce R. Broyles, Oakdale, MN (US)

(*) Notice: Subject to any disclaimer, the term of this patent is extended or adjusted under 35 U.S.C. 154(b) by 193 days.

(21) Appl. No.: 14/531,564

(22) Filed: Nov. 3, 2014

(65) Prior Publication Data
US 2015/0125827 A1 May 7, 2015

Related U.S. Application Data

(60) Provisional application No. 61/900,769, filed on Nov. 6, 2013.

(51) Int. Cl.
*A61C 5/06* (2006.01)
*A61C 5/04* (2006.01)

(52) U.S. Cl.
CPC ............ *A61C 5/062* (2013.01); *A61C 5/04* (2013.01)

(58) Field of Classification Search
CPC ................................. A61C 5/062; A61C 5/04
USPC ................ 433/80, 82, 87, 89; D24/156
See application file for complete search history.

(56) References Cited

U.S. PATENT DOCUMENTS

| | | | |
|---|---|---|---|
| 3,900,954 A | 8/1975 | Dragan | |
| 4,572,210 A | 2/1986 | McKinnon | |
| 4,660,569 A | 4/1987 | Etherington | |
| D292,825 S * | 11/1987 | Dragan | ................ D24/112 |
| 4,972,969 A | 11/1990 | Randklev | |
| 5,061,179 A * | 10/1991 | Dragan | ............ A61O 5/062 433/90 |
| 5,387,103 A | 2/1995 | Fischer | |
| 5,489,207 A | 2/1996 | Dragan | |
| 5,865,803 A | 2/1999 | Major | |

(Continued)

FOREIGN PATENT DOCUMENTS

| | | |
|---|---|---|
| EP | 1591085 | 11/2005 |
| GB | 1475430 | 6/1977 |

(Continued)

OTHER PUBLICATIONS

Filtek™ Z250 Universal Restorative, 3M ESPE product brochure, © 3M 2008, 2 pp.

(Continued)

*Primary Examiner* — Pedro Philogene
*Assistant Examiner* — David C Comstock

(57) ABSTRACT

An apparatus for dispensing a viscous dental paste that includes a barrel member, a dispensing tip, and a platform. The barrel defines a chamber for containing a viscous material. The dispensing tip extends from the barrel member to a dispensing end and defines a passageway open to the chamber. The dispensing end forms an outlet opening open to the passageway and circumscribed by a continuous wall defining an interior surface and an exterior surface. The platform projects from the dispensing end and defines opposing first and second major faces. The first major face is aligned with the outlet opening. The second major face is contiguous with a section of the exterior surface. Viscous material is dispensed from the chamber and onto the platform as a ribbon or sheet.

20 Claims, 10 Drawing Sheets

(56) References Cited

U.S. PATENT DOCUMENTS

| | | | |
|---|---|---|---|
| 6,312,254 B1 * | 11/2001 | Friedman | A61O 5/062 433/32 |
| 6,569,122 B2 | 5/2003 | Fischer | |
| 6,638,065 B2 | 10/2003 | Fischer | |
| 6,916,308 B2 | 7/2005 | Dixon | |
| 6,929,157 B2 | 8/2005 | Orecchia | |
| 1,591,085 A1 | 11/2005 | Kurc | |
| 7,261,559 B2 | 8/2007 | Smith | |
| 7,503,905 B2 | 3/2009 | Jessop | |
| 2002/0076671 A1 | 6/2002 | Evers | |
| 2012/0181300 A1 | 7/2012 | Maxa | |
| 2012/0244493 A1 | 9/2012 | Leiner | |
| 2013/0115568 A1 | 5/2013 | Jelovac | |

FOREIGN PATENT DOCUMENTS

| | | |
|---|---|---|
| JP | 11290345 | 10/1999 |
| WO | WO 2009-029974 | 3/2009 |

OTHER PUBLICATIONS

Filtek™ Supreme Ultra Universal Restorative, 3M ESPE product brochure, © 3M 2010, 6 pp.

* cited by examiner

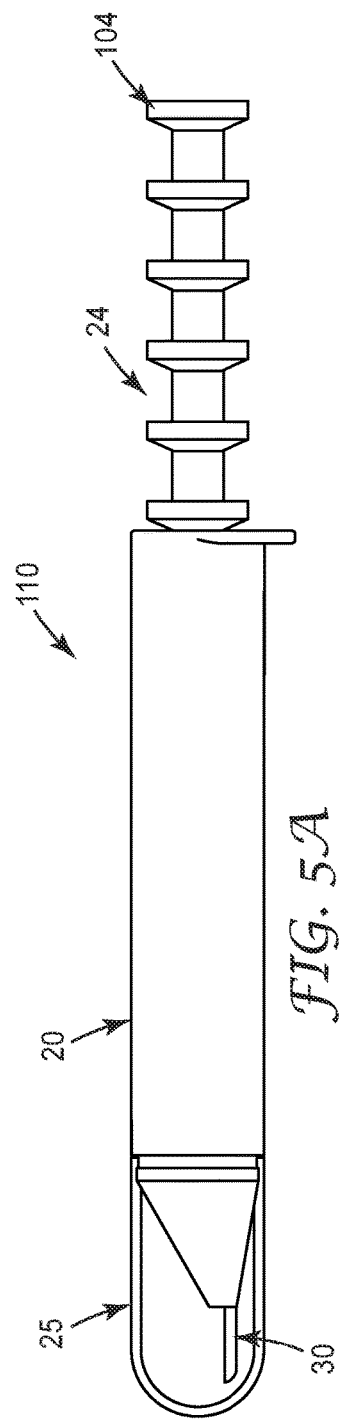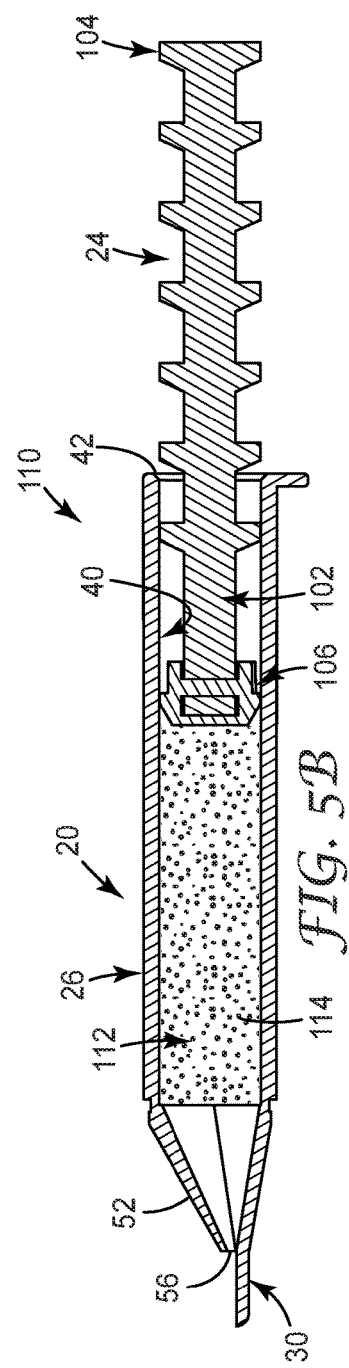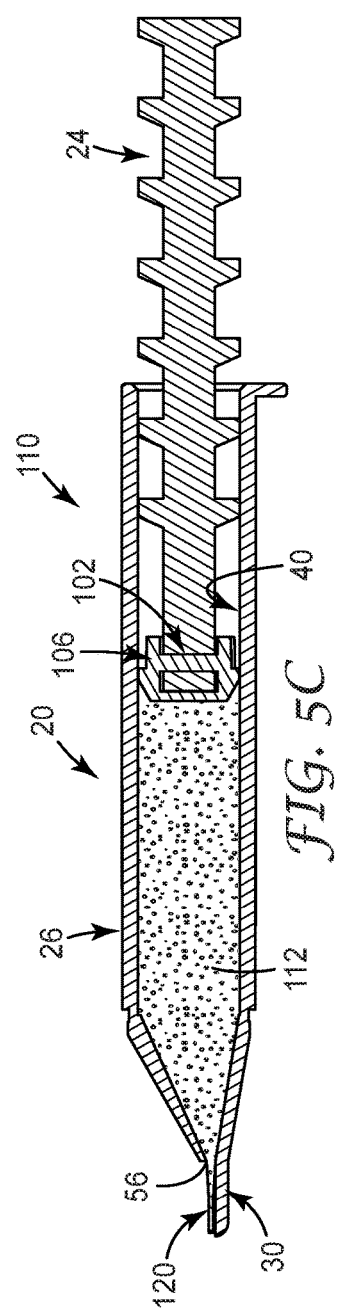

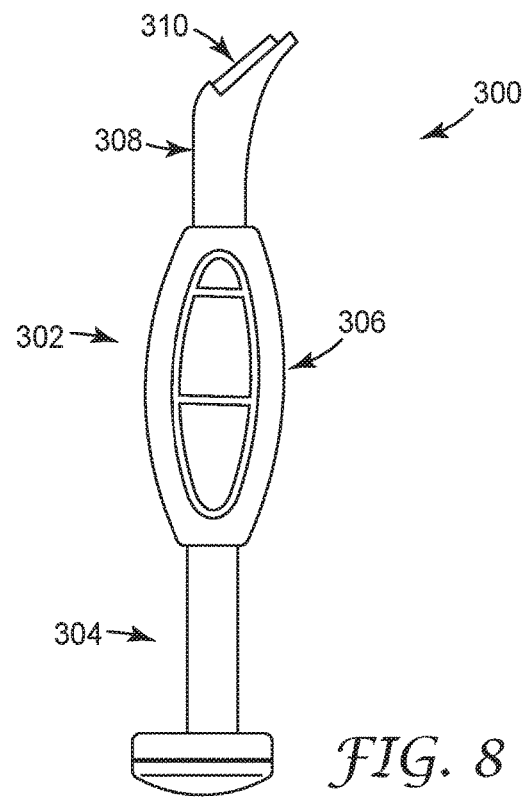
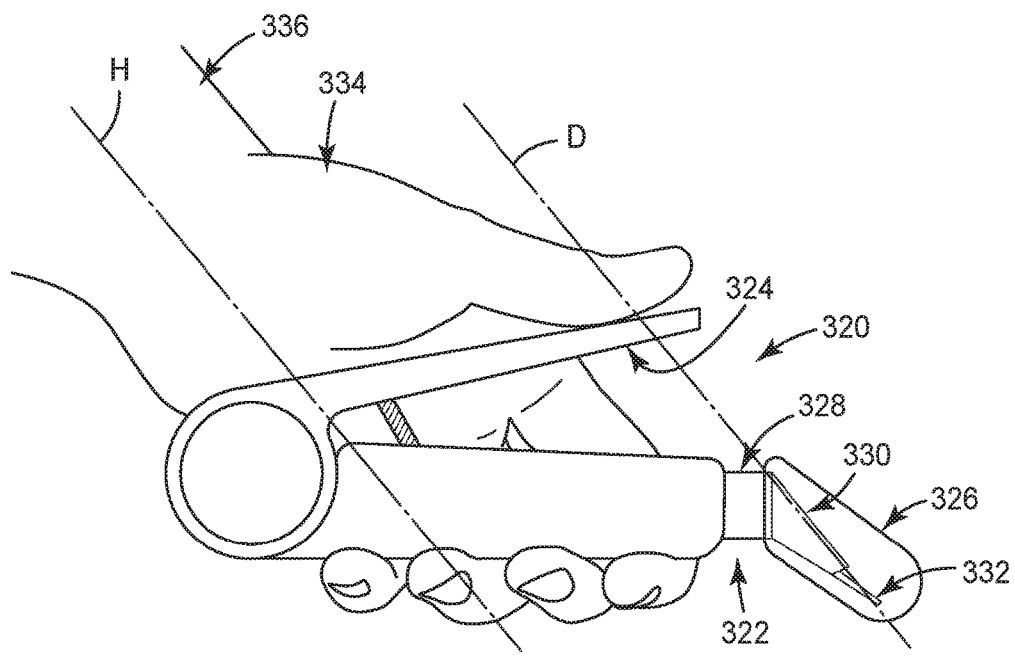

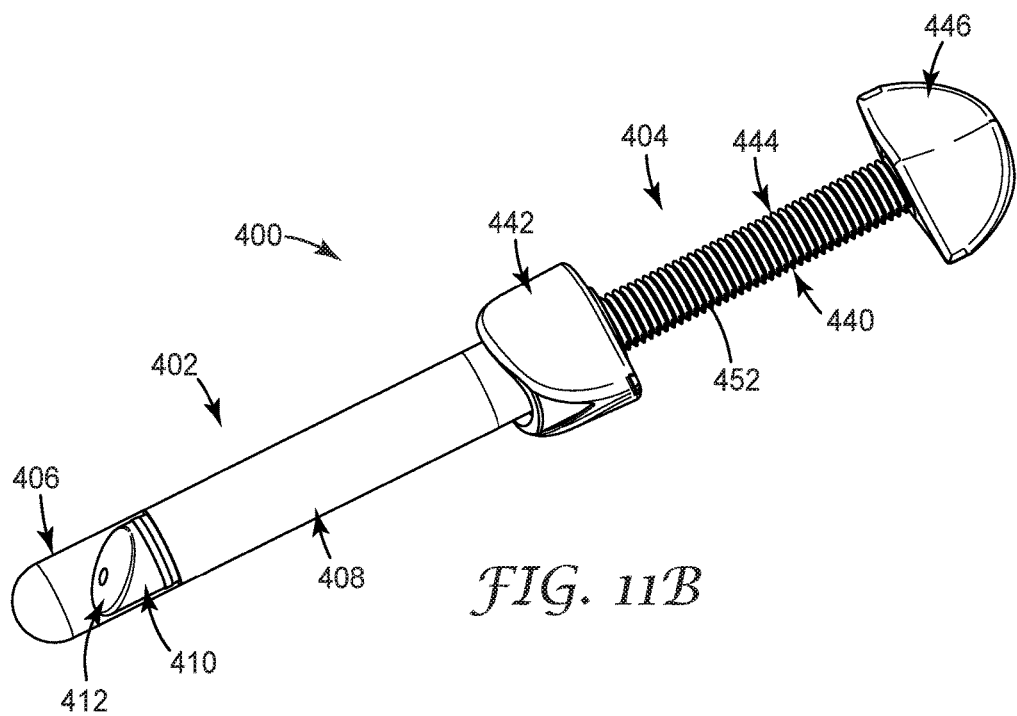
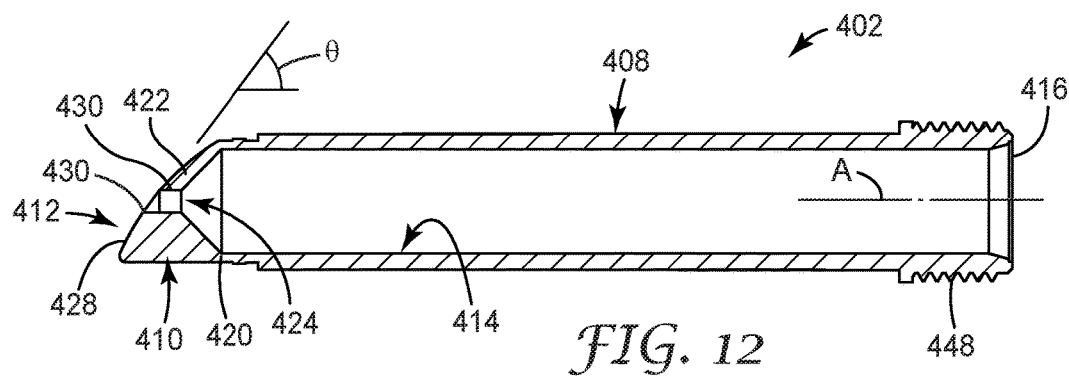
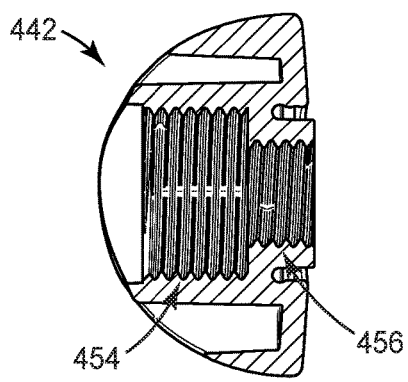

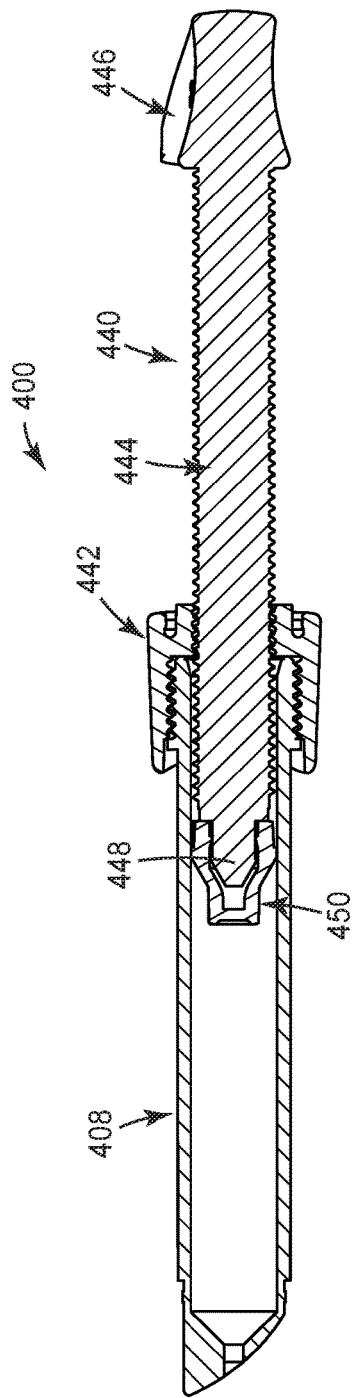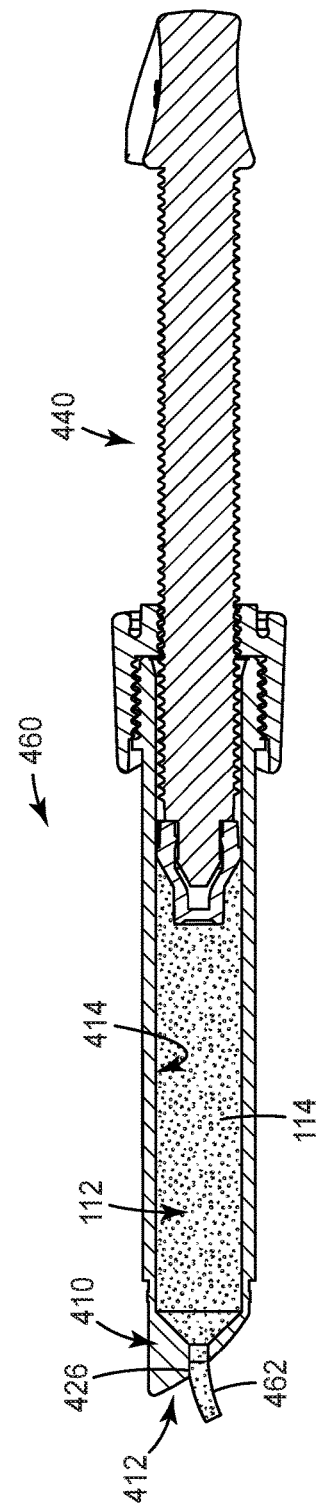

HANDHELD VISCOUS DENTAL PASTE DISPENSER

BACKGROUND

The present disclosure relates to devices for dispensing highly viscous materials, such as viscous dental pastes. More particularly, it relates to handheld, manually operated devices for temporarily storing and selectively dispensing small quantities of viscous dental paste or other highly viscous materials.

Many clinical dental procedures involve the application of a dental composite material onto one or more teeth of the patient. Oftentimes, the dental material is highly viscous immediately prior to application (e.g., restoratives, core build up materials, etc.), and may further harden once applied. These dental materials are thus packaged and provided to the dentist or other end user in a paste-like (i.e., a thickened yet extrudable or pliable solid paste) form. The actual volume or amount of viscous dental paste required for a particular procedure varies from procedure-to-procedure, and most procedures entail sequentially applying small quantities of the dental paste to the same region. For example, an initial source volume or amount of the dental paste is made available to the dentist. The dentist retrieves a small quantity or portion of dental paste from this source volume (e.g., using a spatula or other instrument) and applies it to the patient's tooth (or other oral region). Later, another (and possibly additional) small portion is retrieved from the source volume and applied on top of the first application and/or to other regions in accordance with the procedure's recommended protocol.

In light of the above, viscous dental paste packaging desirably accounts for not only the high viscosity properties of the dental paste, but also normal usages in which the dentist must repeatedly retrieve and apply small amounts of the dental paste from a source volume. Because the application instrument(s) repeatedly contacts the dental paste source volume and the patient's mouth, any unused amount of the dental paste source volume cannot be used with a second patient due to possible cross-contamination concerns and is discarded. Moreover, many dental pastes are radiation-reactive and will solidify with sufficient exposure to ambient light. Once exposed to an excessive amount of ambient light, the dental paste will harden to a point that it is unusable and must be discarded. Thus, simply packaging a large volume of dental paste in a conventional lidded container is impractical. Conversely, because it is effectively impossible to know in advance the exact amount of dental paste needed for a particular procedure and the actual amount used can vary widely for different procedures, a "single use" packaging format is not preferred.

Further, many dental pastes are relatively expensive; the cost savings associated with a more bulk-like packaging format (as compared to single use) are desirable to dentists and their patients.

One well-received viscous dental paste packing format that addresses the above concerns is akin to a conventional syringe. As initially provided to the dentist, the syringe barrel (often formed of a light shielding material) maintains a volume of the dental paste sufficient to perform multiple procedures. The dispensing end of the barrel forms a relatively large opening, appropriate for manually-induced (i.e., manipulation of the syringe's plunger by the dentist's or other user's hand(s)) extrusion or dispensing of a highly viscous paste. Consistent with the above descriptions, while the packaged syringe is relatively small for convenient hand operation and thus the initial volume of contained viscous dental paste is also relatively small, most cosmetic and/or functional augmentation procedures require only a small portion of the packaged volume. As such, typically only a small quantity of the viscous dental paste is dispensed from the syringe in a progressive manner for each individual procedure. Although any unused amount of the dispensed dental paste is discarded, the volume still contained within the syringe is available for subsequent procedures. The syringe packaging format beneficially affords the dentist the ability to control the amount of dental paste actually dispensed for each procedure.

Because the dental paste is highly viscous, as it extrudes from the syringe barrel, the extruded strand will initially stay "connected" to the syringe (i.e., does not drip or immediately fall from the syringe barrel). While it may be possible to apply the dispensed quantity directly onto the patient's tooth as it is extruded from the syringe, most dentists highly prefer to employ a separate instrument, such as a spatula, to apply the material. With this in mind, the dentist will normally extrude and then "wipe" a small quantity of the viscous dental paste from the syringe onto a clean pad. The spatula or other instrument is utilized to retrieve small amounts of the dispensed quantity from the pad and then apply the retrieved dental paste to the patient's mouth. While viable, the amount of dispensed dental paste required by this technique is typically larger than actually needed for the procedure, leading to waste. Alternatively or in addition, the dentist may use the spatula to retrieve or "dig" a small amount from the extruded strand still "connected" to the syringe. This approach can lead to cross-contamination concerns, especially if the dentist inadvertently inserts the spatula into the relatively large barrel opening.

The highly viscous nature of many dental pastes in combination with normal procedures for dispensing small quantities of the material render current syringe-like packaging formats less than optimal. It is difficult to dispense only a small amount of the dental paste from the syringe, and existing syringe formats may encourage actions giving rise to cross-contamination concerns. Thus, a need exists for a viscous dental paste dispensing apparatus that maintains a bulk supply of dental paste, and facilitates safe and easy retrieval of smaller amounts by the dentist with minimal waste.

SUMMARY

Some aspects of the present disclosure relate to an apparatus for dispensing a viscous dental paste. The apparatus includes a barrel member, a dispensing tip, and a platform. The barrel member defines a chamber for maintaining a viscous material. The dispensing tip extends from the barrel member and defines a passageway open to the chamber. The dispensing tip terminates at a dispensing end opposite the barrel member. The dispensing end forms an outlet opening that is open to the passageway and is circumscribed by a continuous wall defining an interior surface and an exterior surface. The platform projects from the dispensing end and defines opposing first and second major faces. The first major face is arranged to receive material dispensed through the outlet opening. The second major face is contiguous with a section of the exterior surface. With this construction, viscous material is dispensed from the chamber and onto the platform via the dispensing tip, with the platform supporting the dispensed material for subsequent retrieval by a user. In some embodiments, the apparatus further includes a plunger, with the apparatus being akin to a syringe. In other embodiments, the dispensing tip defines a tapering shape in extension to the dispensing end, configured to extrude a sheet or ribbon onto the platform.

Other aspects of the present disclosure relate to a viscous paste packaged article. The packaged article includes a dispensing apparatus and a volume of viscous paste. The dispensing apparatus includes a barrel member, a dispensing tip, and a platform. The barrel member defines a chamber. The dispensing tip extends from the barrel member and defines a passageway open to the chamber. The dispensing tip terminates at a dispensing end opposite the barrel member. The dispensing end forms an outlet opening. The outlet opening is open to the passageway and is circumscribed by a continuous wall defining an interior surface and an exterior surface. The platform projects from the dispensing end and defines opposing first and second major faces. The first major face is aligned with the outlet opening. The second major face is contiguous with a section of the exterior surface. The volume of viscous paste is temporarily contained within the chamber. With this construction, a quantity of the volume of viscous paste can be dispensed onto the platform from the chamber and is exteriorly accessible. In some embodiments, the viscous paste is a highly viscous dental paste such as a restorative dental composition.

BRIEF DESCRIPTION OF THE DRAWINGS

FIG. 5A is a side view of a viscous paste packaged article in accordance with principles of the present disclosure, including the apparatus of FIG. 1 upon final assembly;

FIG. 5B is a longitudinal cross-sectional view of the packaged article of FIG. 5A;

FIG. 5C is a longitudinal cross-sectional view of the packaged article of FIG. 5B and illustrating operation of the article in dispensing a viscous paste;

FIG. 8 is a side view of another embodiment viscous paste dispensing apparatus;

FIG. 9 is a side view illustrating use of another viscous paste dispensing apparatus in accordance with principles of the present disclosure;

FIG. 11B is a perspective view of the apparatus of FIG. 11A upon final assembly;

FIG. 12 is a cross-sectional view of a barrel component of the apparatus of FIG. 11A;

FIG. 13 is a cross-sectional view of a collar component of the apparatus of FIG. 11A;

FIG. 14 is a cross-sectional view of the apparatus of FIG. 11B; and

FIG. 15 is a cross-sectional view of a viscous paste packaged article in accordance with principles of the present disclosure, including the dispensing apparatus of FIG. 14.

DETAILED DESCRIPTION

Figure 1:
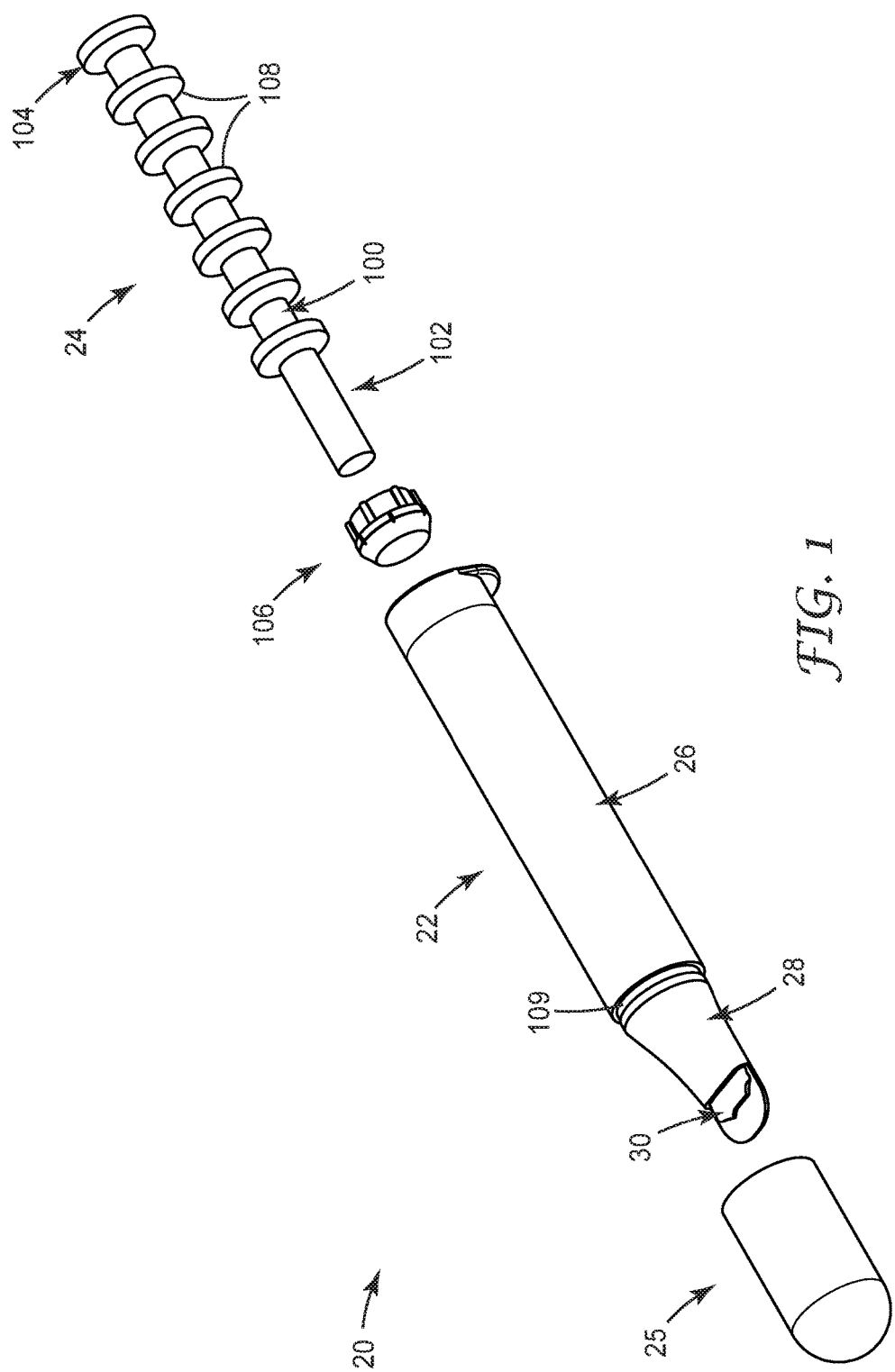
FIG. 1 is an exploded perspective view of a viscous paste dispensing apparatus in accordance with principles of the present disclosure.

One embodiment of an apparatus 20 for dispensing a viscous dental paste in accordance with principles of the present disclosure is shown in FIG. 1. The apparatus 20 includes a barrel 22, an optional plunger 24, and an optional cap 25. Details on the various components are provided below. In general terms, however, the barrel 22 includes or forms a barrel member 26, a dispensing tip 28, and a platform 30. The plunger 24, where provided, is slidably connected to the barrel 22, with the apparatus 20 operable to dispense a quantity of viscous paste or other highly viscous material (not shown) stored in the barrel member 26 onto the platform 30 for convenient access by a dentist or other user. Where provided, the optional cap 25 can cover the platform 30 during periods of non-use. As described below, loading the dispensing apparatus 20 with a dental paste provides a dental paste packaged article in accordance with principles of the present disclosure.

The barrel 22 can assume a variety of forms and in some embodiments integrally or homogeneously forms the barrel member 26, the dispensing tip 28, and the platform 30 (e.g., the barrel 22 is an integrally molded plastic body). In other embodiments, one or more of the components 26-30 can be separately formed and subsequently assembled. With this in mind, the barrel 22 is shown in greater detail in FIG. 2, and illustrates that the barrel member 26 forms a chamber 40. The chamber 40 can have a uniform diameter sized in accordance with a corresponding feature of the plunger 24 (FIG. 1), and is open at a terminal end 42 of the barrel member 26. In this regard, the terminal end 42 can form or include features conducive to handling or operation by a user, such as a flange 44. Regardless, the chamber 40 is sized to contain a volume of viscous paste or other highly viscous material as described below. With embodiments in which the apparatus 20 (FIG. 1) is akin to a syringe, the barrel member 26 can be an elongated cylinder, and defines a central axis A. Remaining features of the barrel 22 can be described with respect to the central axis A.

The dispensing tip 28 extends from the barrel member 26 in a direction of the longitudinal axis A, and defines a trailing end 50 and a dispensing end 52. The trailing end 50 is formed at the intersection of the dispensing tip 28 with the barrel member 26, and thus defines a diameter (or other dimension) in accordance with the diameter of the barrel member 26. Further, the dispensing tip 28 forms a passageway 54 that is fluidly open to the chamber 40. The passageway 54 is continuous to the dispensing end 52, and is fluidly open to an exterior of the barrel 22 at an outlet opening 56 at the dispensing end 52.

Figure 3:
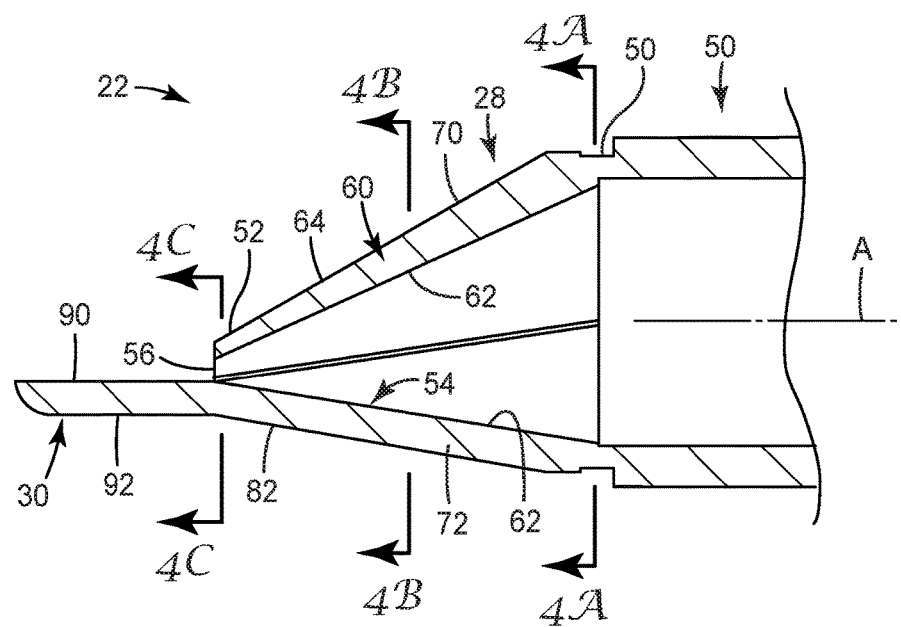
FIG. 3 is an enlarged cross-sectional view of a portion of the barrel of FIG. 2.

As more clearly illustrated in FIG. 3, the dispensing tip 28, including the passageway 54, can taper from the trailing end 50 to the dispensing end 52. The tapered shape of the dispensing tip 28 can be described, for example, relative to an exterior thereof. For example, the dispensing tip 28 can be formed or defined by a continuous wall 60 defining an interior surface 62 and an exterior surface 64. The interior surface 62 defines the confines of the passageway 54, whereas the exterior surface 64 is separated from the passageway 54 by a thickness of the wall 60. With this in mind, and relative to the upright orientation reflected in FIG. 3 (in which the central axis A is horizontally arranged), the wall 60 can be viewed as having an upper segment 70 and a lower segment 72 in longitudinal cross-section. The tapering shape of the dispensing tip 28 can include the upper segment 70 projecting toward the lower segment 72 (e.g., vertically downward toward the central axis A relative to the orientation of FIG. 3) in extension from the trailing end 50 to the dispensing end 52. The lower segment 72 optionally includes a slight vertically upward component in extension to the dispensing end 52 as shown. Regardless, the shape of the passageway 54 (as defined by the interior surface 62) tapers in a corresponding fashion.

Figure 2:
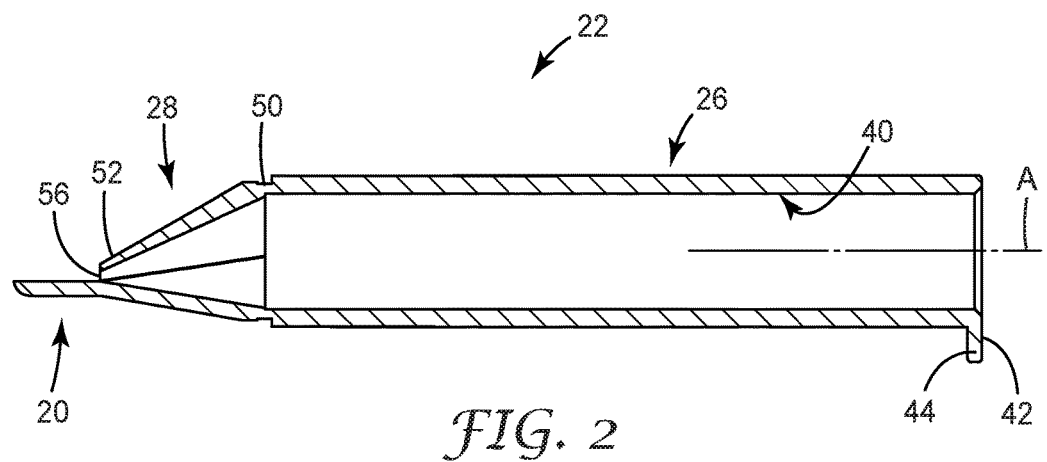
FIG. 2 is a longitudinal cross-sectional view of a barrel component of the apparatus of FIG. 1.

While the dispensing tip 28 can taper in the vertical direction (relative to the orientation of FIG. 3) as shown, the dispensing tip 28 may exhibit little, if any, taper in the horizontal direction. For example, FIG. 4A reflects a transverse cross-sectional shape (i.e., in a plane perpendicular to the central axis A (FIG. 3)) of the dispensing tip 28 at or immediately proximal the trailing end 50. The passageway 54 can have the circular shape as shown, commensurate with a shape of the chamber 40 (FIG. 2) of the barrel member 26 (FIG. 2). Vertical and horizontal dimensions V, H of the passageway 54 are identified in FIG. 4A, and can be identical at the trailing end 50 (where the passageway 54 optionally is a true circle in transverse cross-section). FIG. 4B reflects a shape of the passageway 54 intermediate the trailing and dispensing ends 50, 52 (FIG. 3). As reflected by a comparison of FIGS. 4A and 4B, the passageway 54 has transitioned to a more oblong shape in transverse cross-section, with the vertical dimension V being reduced whereas the horizontal dimension H is substantially unchanged. Finally, FIG. 4C illustrates the dispensing tip 28 at or immediately adjacent the dispensing end 52. The passageway 54 has a further reduced vertical dimension V and a substantially unchanged horizontal dimension H (as compared to shapes of FIGS. 4A and 4B).

As reflected by FIG. 4C, the outlet opening 56 is circumscribed by the wall 60. As a point of reference, FIG. 4C is a cross-section taken at the dispensing end 52 and at which the passageway 54 terminates at or is defined by the outlet opening 56; thus, both the passageway 54 and the outlet opening 56 can be identified in FIG. 4C. The elongated, optionally obround, shape can be defined (in the transverse cross-section plane perpendicular to central axis A (FIG. 3)) as having opposing, first and second sides 80, 82 and opposing, first and second ends 84, 86. The sides 80, 82 can be relatively flat (at least along the interior surface 62), and define a horizontal dimension H that is greater than a vertical dimension V defined by the ends 84, 86. In some embodiments, the horizontal dimension H of the sides 80, 82 is at least five times greater than the vertical dimension of the ends 84, 86.

Figure 4A:
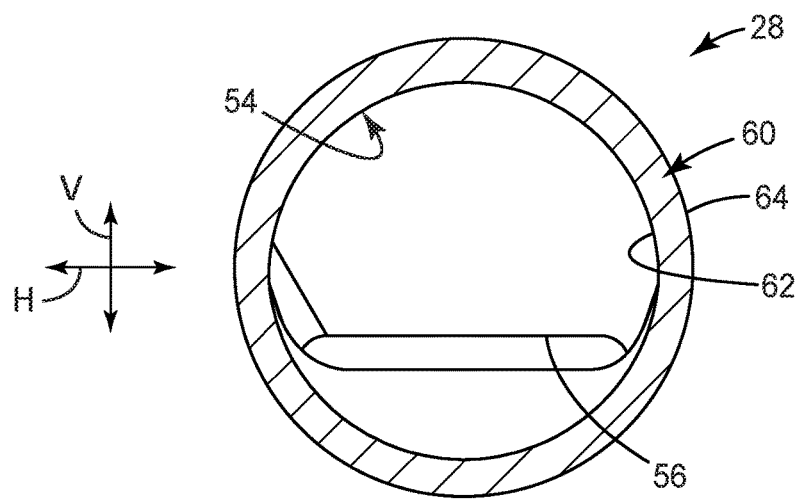
FIG. 4A is a transverse cross-sectional view of the barrel of FIG. 3, taken along the line 4A-4A.
Figure 4B:
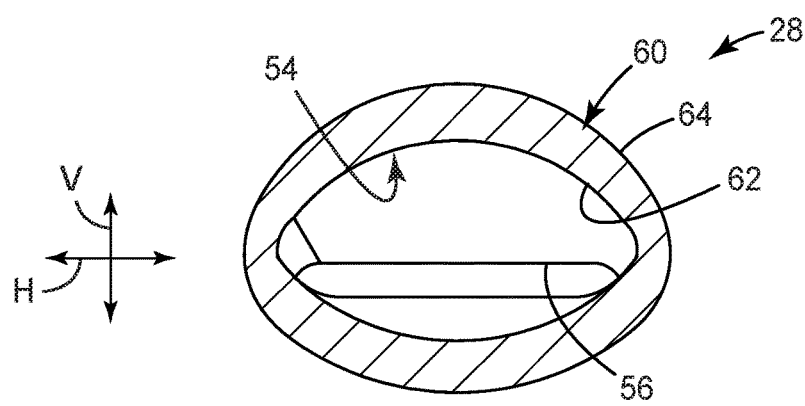
FIG. 4B is a transverse cross-sectional view of the barrel of FIG. 3, taken along the line 4B-4B.
Figure 4C:
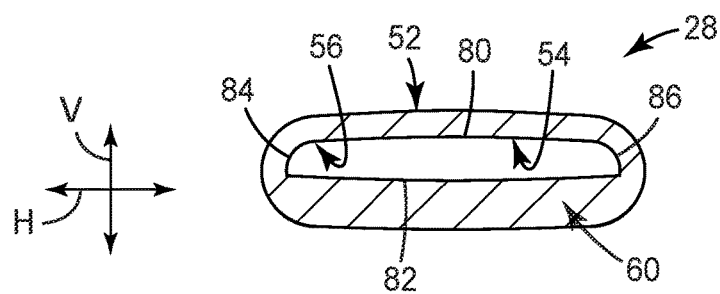
FIG. 4C is a transverse cross-sectional view of the barrel of FIG. 3, taken along the line 4C-4C.

Tapering of the dispensing tip passageway 54 to the dispensing end 52 can assume other forms that may or may not be implicated by the shapes of FIGS. 4A-4C, and the outlet opening 56 can have other transverse cross-sectional shapes (in a plane perpendicular to the central axis A (FIG. 3)). In some embodiments, however, the transverse cross-sectional area of the outlet opening 56 is less than a transverse cross-sectional area of the chamber 40 (FIG. 2), and has a relatively elongated perimeter shape in the transverse plane (e.g., plane perpendicular to the central axis A) that differs from the transverse perimeter shape of the chamber 40. By way of comparison, the chamber 40 can have a circular or other non-elongated transverse perimeter shape. Regardless, the elongated transverse perimeter shape of the outlet opening 56 dictates that material forced through the outlet opening 56 will have a flattened, ribbon or sheet-like shape (as compared to an optional transverse shape of the chamber 40 that forces contained material to a cylindrical shape) in some embodiments.

As reflected by FIGS. 2-4C, the passageway 54 is entirely continuous or open from the chamber 40 to the outlet opening 56 in some embodiments. That is to say, with some constructions of the present disclosure, the dispensing tip 28 does not include or provide any internal walls or other structures that might otherwise interrupt or divide the passageway 54. With these optional embodiments, then, the outlet opening 56 serves as the only opening through which material from the chamber 40 can be dispensed and is continuously open within the confines of the interior surface 62.

Returning to FIG. 3, the platform 30 projects from the dispensing end 52 of the dispensing tip 28 immediately adjacent or immediately distal the outlet opening 56, and defines opposing, first and second major faces 90, 92. The first major face 90 is aligned with a portion of the interior surface 62 of the dispensing tip 28, and the second major face 92 is aligned with a portion of the exterior surface 64. More particularly, the platform 30 can be viewed as a continuous extension of the second side 82 of the outlet opening 56 perimeter, with the second major face 92 being contiguous with the exterior surface 64 at the second side 82, and the first major face 90 being contiguous with the interior surface 62 at the second side 82.

In some embodiments, the platform 30 is relatively planar, with at least the first major face 90 being substantially flat (e.g., within 5% of a truly flat surface). The horizontal width of the first major face 90 is commensurate with that of the outlet opening 56 such that material dispensed through the outlet opening 56 can be fully supported by the platform 30. Other geometric features of the platform 30 can assume a variety of forms. For example, in some embodiments, the platform 30 terminates in a rounded edge opposite the dispensing tip 28. Further, the second major face 92 can optionally be substantially flat as shown. Regardless, the first major face 90 defines an available surface area for receiving material dispensed from the outlet opening 56, with the platform 30 robustly supporting and exteriorly exposing an entirety of the dispensed material (e.g., the platform 30 is not partially covered). In some embodiments, a surface area of the first major face 90 is relatively small (e.g., on the order of 50 mm$^2$), and thus encourages the dentist or other user to limit the amount of material dispensed (i.e., the quantity of dispenses material will not exceed a surface area size of the platform 30). This feature, in turn, can inherently minimize waste.

Returning to FIG. 1, the plunger 24 can have a variety of forms useful for interfacing with the barrel 22, and in particular the barrel member 26. In general terms, the plunger 24 includes a shaft 100 extending between a piston end 102 and a handle end 104. As with conventional syringe designs, the piston end 102 is sized and shaped to be slidably disposed within the chamber 40 (FIG. 2) in a sealed-type fashion, for example via a distal seal member 106. The handle end 104 can have a variety of configurations, and is generally constructed to provide a convenient surface for a user-applied force. In some embodiments, the plunger 24 can incorporate additional components or mechanisms that facilitate movement of the piston end 102 in response to a user-applied force at the handle end 104, for example intermediate discs 108 that are described below. In other embodiments, the plunger 24 can be configured to translate a turning or twisting force applied at the handle end 104 into a longitudinal movement of the piston end 102. Alternatively, the plunger 24 can have a more simplified form, consisting of the shaft 100, a sealing member on or adjacent one end, and a handle on or adjacent the opposite end.

The cap 25, where provided, is configured to be selectively assembled over the platform 30 and at least a portion of the dispensing tip 28. When so-assembled, the cap 25 effectively shields or seals the outlet opening 56. Thus, during periods of non-use, the cap 25 can be installed to protect the viscous material (not shown) contained in the barrel member 26 from the external environment. In some embodiments, the barrel 22 can form or provide a groove 109 or feature for selectively retaining the cap 25 in a snap fit-type relationship. As a point of reference, FIG. 1 reflects the cap 25 as being transparent or substantially transparent. With this but one acceptable embodiment, a user can more readily visualize an interior of the cap 25 when installed over the platform 30, for example to determine if any viscous material remains on the platform 30. In related embodiments, the transparency and color of the cap 25 is selected to protect the particular viscous dental paste (not shown) packaged within the apparatus 20 from specific wavelengths of light. As described below, some viscous dental pastes useful with the present disclosure are light radiation curable, for example formulated to be activated by blue light. The cap 25 can be a transparent orange, transparent yellow or transparent red plastic selected to filter blue light (it being understood that other color filtration can be implemented as a function of the photo-initiator absorption characteristics of the particular paste). Under these circumstances, "exposed" light radiation curable material on the platform 30 can be safely protected from actinic light rays within the cap 25 while the apparatus 20 is stored between uses. Prior to the next use, a user can readily "see" the material on the platform 30 through the cap 25 and know in advance whether any additional material needs to be dispensed. Alternatively, the cap 25 can have a wide variety of other constructions. In yet other embodiments, the cap 25 is omitted.

Final assembly of the dispensing apparatus 20 as part of a viscous paste packaged article 110 is reflected in FIGS. 5A and 5B. As shown in FIG. 5B, viscous paste 112 is loaded within the chamber 40 to define a packaged supply volume 114 of the viscous paste 112. The piston end 102/seal member 106 is also disposed within the chamber 40, and prevents release of the viscous paste 112 from the terminal end 42. FIG. 5A further reflects removable assembly of the cap 25 over the platform 30.

During use, a quantity or portion of the supply volume 114 of the viscous paste 112 can be incrementally dispensed from the apparatus 20 by actuation of the plunger 24. In this regard, and as mentioned above, the plunger 24 can assume a variety of forms capable of transferring a user-applied force at the handle end 104 into movement of the piston end 102 (and thus seal member 106). Regardless of the exact plunger 24 configuration, movement of the seal member 106 forces the supply volume 114 of the viscous paste 112 toward the dispensing end 52. As shown in FIG. 5C, a ribbon or sheet 120 of the viscous paste 112 is dispensed or extruded through the outlet opening 56 (due to the elongated transverse shape of the outlet opening 56 as described above). In some embodiments, the dispensing apparatus 20 is configured such that only a single ribbon 120 is dispensed, and is entirely uncovered (apart from the platform 30) and thus easily accessible from an exterior of the apparatus 20. The ribbon 120 is supported or held by the platform 30, but is otherwise accessible by a user. Using a spatula (not shown) or similar instrument, a small portion of the viscous paste 112 can be incrementally removed from the ribbon 120 and applied to the patient. In this regard, the platform 30 provides a robust surface against which the spatula or other instrument can be pressed when retrieving the small portions (e.g., in a digging or cutting-like motion). The platform 30 assists the user in maintaining a clean environment and in dispensing only a relatively small amount of the viscous paste 112, thereby minimizing waste.

The viscous paste or highly viscous material 112 can assume a wide variety of forms and in some embodiments is a viscous dental paste. Typical dental restorative compositions or pastes include, for example, Filtek™ Z250 Universal Restorative and Filtek™ Supreme Universal Restorative, available from 3M Company, St. Paul, Minn. In some embodiments, the viscous dental paste is radiation-reactive (i.e., light radiation curable). With these and similar embodiments, components of the dispensing apparatus 20 (e.g., the barrel member 26) can be formed from a material(s) selected to block light from interacting with the viscous paste 112 contained within the chamber 40.

Figure 6:
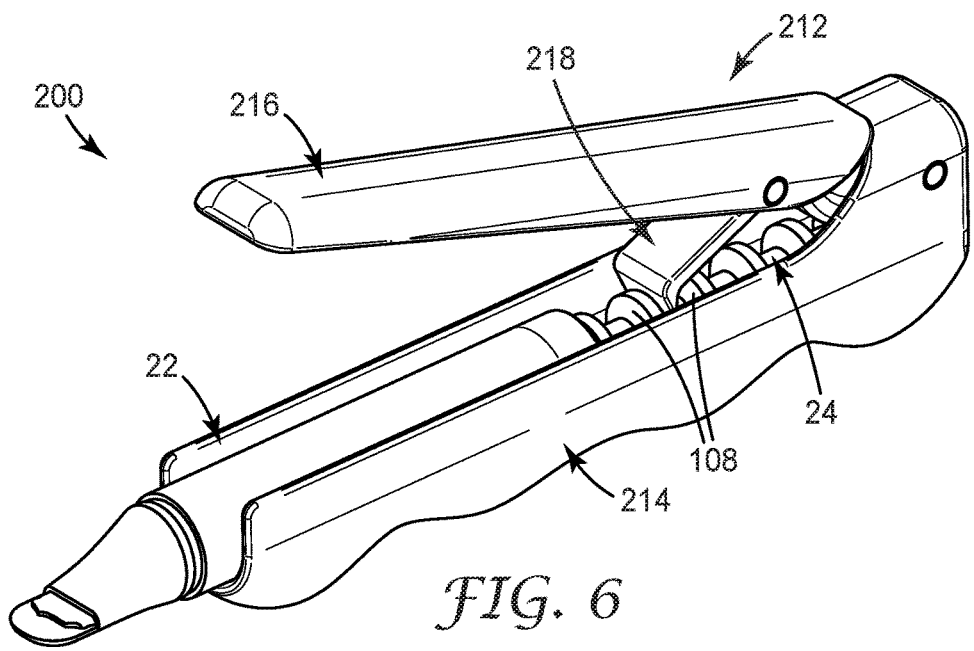
FIG. 6 is a perspective view of another embodiment viscous paste dispensing apparatus in accordance with principles of the present disclosure.

As indicated by the above explanations, some aspects of the present disclosure entail the dispensing of a single sheet or ribbon of viscous paste directly on to a single platform. With this in mind, other features of the apparatus 20 can assume a variety of forms. For example, FIG. 6 illustrates an alternative dispensing apparatus 200 in accordance with principles of the present disclosure and useful as part of a viscous paste packaged article. The apparatus 200 is akin to the apparatus 20 (FIG. 1), and includes the barrel 22 and the plunger 24 described above. Further, the optional cap 25 (FIG. 1) can be provided. Regardless, the dispensing apparatus further includes an actuation mechanism 212 (referenced generally) configured to maintain the barrel 22 and selectively advance the plunger 24. The mechanism 212 includes a grip body 214, a lever arm 216 and a pawl 218. The grip body 214 is sized and shaped to receive the barrel 22 and the plunger 24 (as assembled to the barrel 22). The lever arm 216 is pivotably coupled to the grip body 214, and maintains the pawl 218. The pawl 218, in turn, is configured to interface with selective ones of the intermediate discs 108. As the lever arm 216 is compressed (by hand) toward the grip body 214, the pawl 218 is driven toward the barrel 22; the plunger 24 is forced to move in a similar fashion via interface between the pawl 218 and the particular intermediate disc 108. At the end of the driving motion, the lever arm 216 is can be lifted away from the grip body 214, the pawl 218 freely maneuvered into engagement with another one of the intermediate discs 108, and the process repeated.

Figure 7:
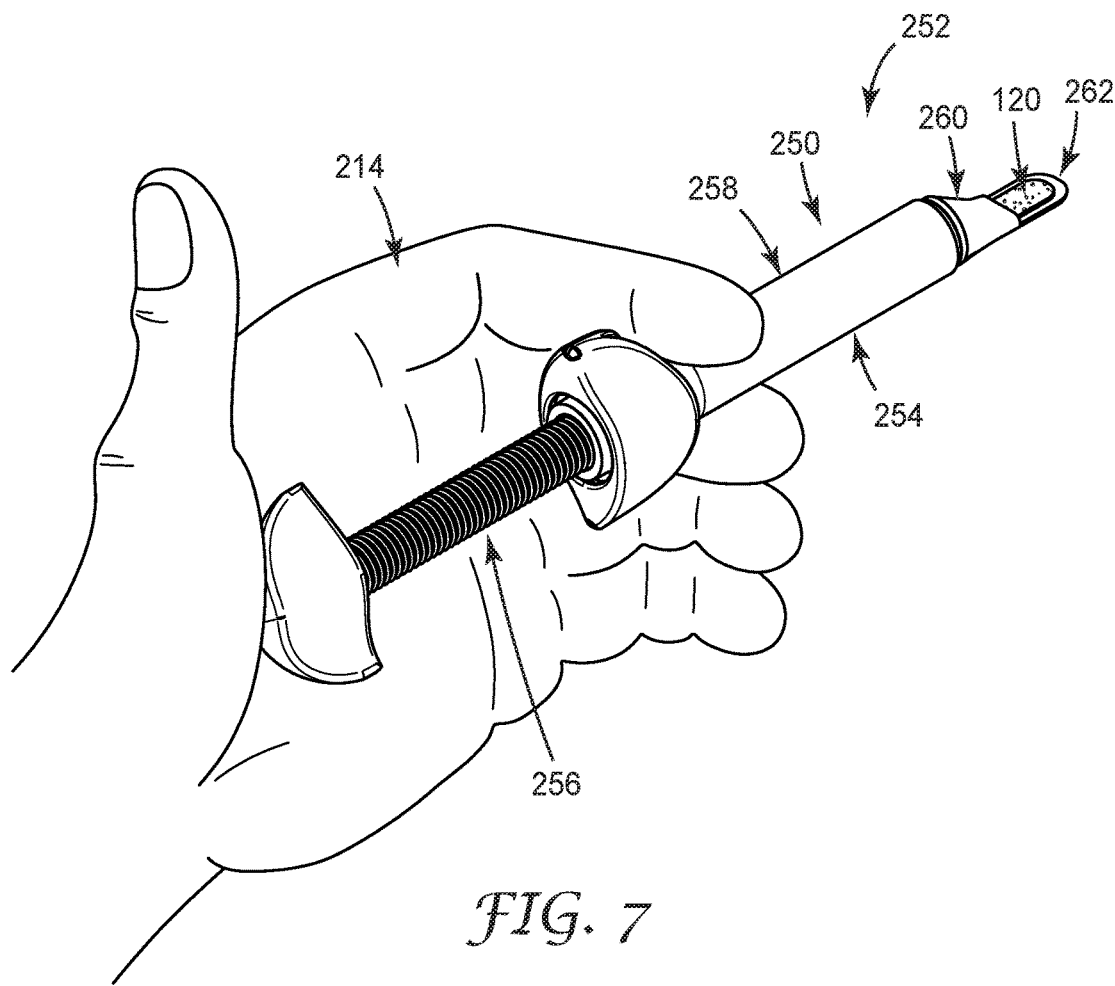
FIG. 7 is a perspective view illustrating use of another viscous paste packaged article in accordance with principles of the present disclosure, including another embodiment viscous paste dispensing apparatus.

Another embodiment dispensing apparatus 250 useful as part of a viscous paste packaged article 252 in accordance with principles of the present disclosure is shown in FIG. 7. The apparatus 250 includes a barrel 254 and a plunger 256. The barrel 254 includes a barrel member 258, a dispensing tip 260, and a platform 262. The barrel member 258 forms a chamber (not shown) within which a portion of the plunger 256 is slidably disposed. The dispensing tip 260 extends from the barrel member 258, and the platform 262 projects from the dispensing commensurate with the above descriptions. The plunger 256 incorporates various features for effectuating movement thereof relative to the barrel 254 by a user's hand 272, for example a twisting motion as indicated by arrows in FIG. 7. Regardless, the platform 262 is located to receive and support the ribbon or sheet of viscous paste 120 extruded from the dispensing tip 260 during operation of the plunger 256.

Another embodiment dispensing apparatus 300 in accordance with principles of the present disclosure and useful as part of a viscous paste packaged article is shown in FIG. 8. The apparatus 300 includes a barrel 302 and a plunger 304. The barrel 302 includes a barrel member 306, a dispensing tip 308, and a platform 310. The barrel member 306 has a contoured shape for grasping by a user's hand (not shown), and forms a chamber (not shown) within which a portion of the plunger 304 is slidably disposed. The dispensing tip 308 extends from the barrel member 306, and the platform 310 projects from the dispensing tip 308. In this regard, the platform 310 can extend in an angular fashion relative to the dispensing tip 308 as shown, and provides a surface for receiving and supporting a ribbon or sheet of dispensed viscous paste commensurate with the descriptions above. The angled arrangement of the platform 310 can promote more ergonomic handling of the apparatus 300 when dispensing and removing dental paste.

The possible ergonomic advantages presented by the angled arrangement described above are further evidenced by another embodiment dispensing apparatus 320 of FIG. 9 in accordance with principles of the present disclosure and useful as part of viscous paste packaged article. The apparatus 320 includes a barrel 322 (referenced generally), a plunger (hidden), an optional actuation mechanism 324, and an optional cap 326. The barrel 322 includes or forms a barrel member 328, a dispensing tip 330 and a platform 332. As shown, the dispensing tip 330 extends at an angle from the barrel member 328 (e.g., a central axis of the dispensing tip 330 is non-parallel with a central axis of the barrel member 328). The platform 332 continues the angled orientation of the dispensing tip 330.

The actuation mechanism 324 can assume a variety of different configurations adapted to facilitate movement of the plunger (not shown) within the barrel member 328 in dispensing a contained viscous paste (now shown) from the dispensing tip 330 and onto the platform 332 when manipulated by a user's hand 334. In this regard, the angled relationship of the dispensing tip 330 relative to the barrel member 328 is such that when the barrel member 328 is naturally held in the user's hand 334 (either alone or as assembled within the actuation mechanism 324), a dispensing axis or angle D established by the dispensing tip 330 generally corresponds with a handling axis or angle H of the user's hand 334 (e.g., the handling axis H passes through a wrist 336 of the user). For example, the dispensing angle D and the handling angle H can be substantially parallel (e.g., within 10% of truly parallel relationship).

Figure 10:
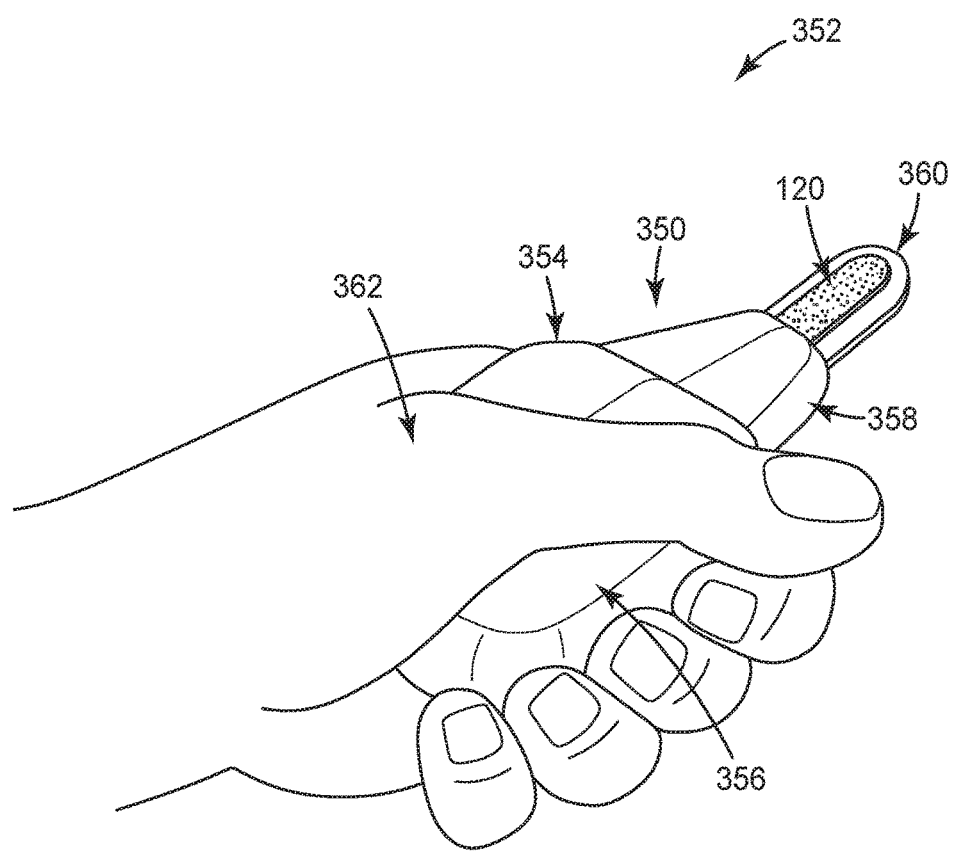
FIG. 10 is a perspective view illustrating use of another viscous paste packaged article in accordance with principles of the present disclosure, including another embodiment viscous paste dispensing apparatus.

Another embodiment dispensing apparatus 350 useful as part of a viscous paste packaged article 352 in accordance with principles of the present disclosure is shown in FIG. 10. The apparatus 350 again includes a barrel 354. The barrel 354 forms or defines a barrel member 356, a dispensing tip 358, and a platform 360. With the embodiment of FIG. 10, the barrel member 356 is akin to a squeeze bottle, and is formed of a thin walled, flexible material conducive to repeated deflection when squeezed by a user's hand 362. Thus, with the dispensing apparatus 350 of FIG. 10, a separate plunger is not included. However, the dispensing tip 358 tapers in extension from the barrel member 356, and the platform 360 extends from the dispensing tip 358 for receiving the ribbon or sheet of viscous paste 120 extruded from the dispensing tip 358.

Figure 11A:
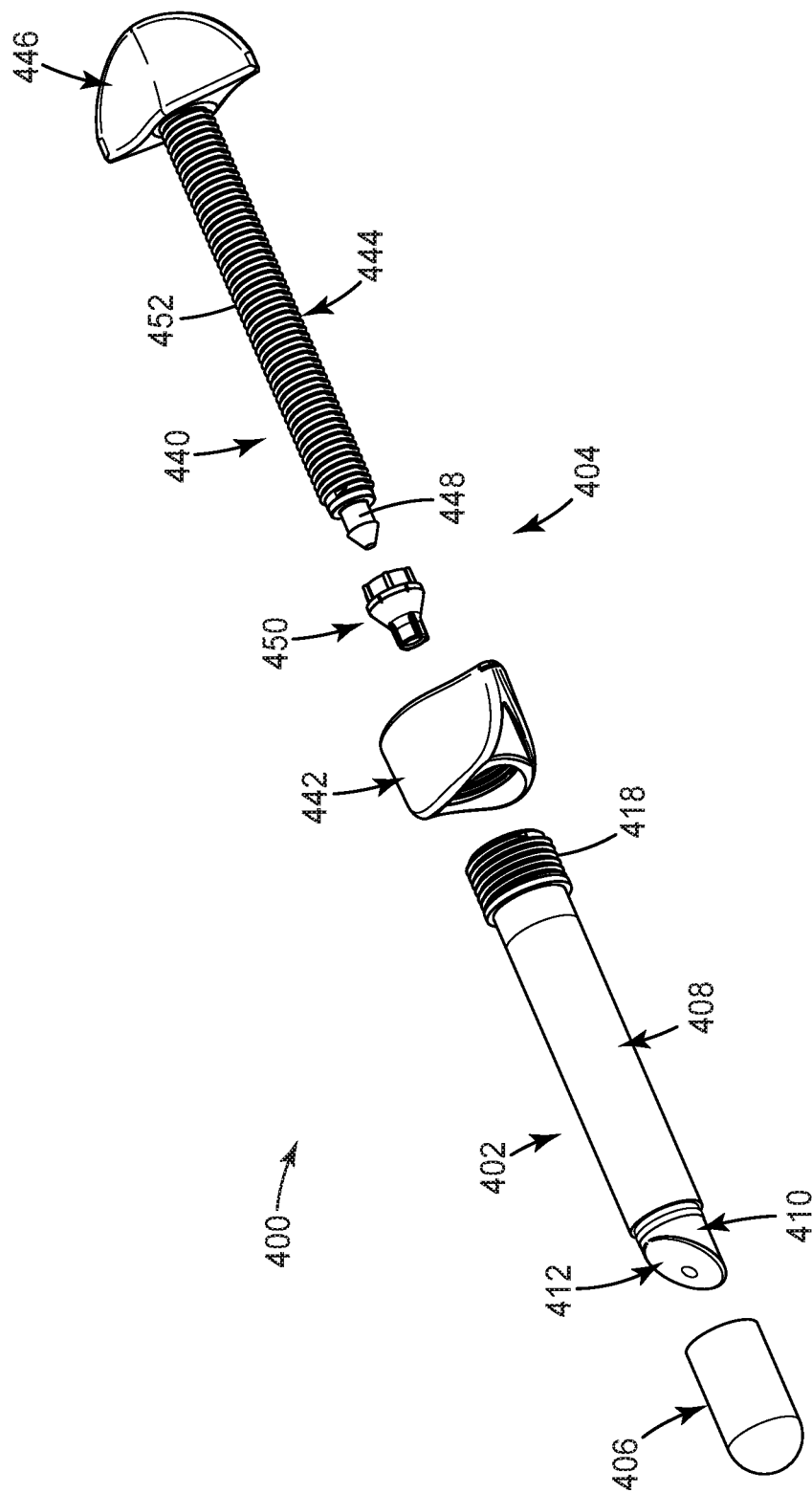
FIG. 11A is an exploded, perspective view of another viscous paste dispensing apparatus in accordance with principles of the present disclosure.

Another embodiment viscous paste dispensing apparatus 400 in accordance with principles of the present disclosure is shown in FIGS. 11A and 11B. The apparatus 400 includes a barrel 402, a plunger assembly 404 and an optional cap 406. As with other embodiments, the plunger assembly 404 is connected to the barrel 402 to facilitate dispensement of a contained viscous material (not shown) from the barrel 402.

The barrel 402 includes or defines a barrel member 408, a dispensing tip 410 and a platform 412. With additional reference to FIG. 12, the barrel member 408 forms a chamber 414 that is otherwise open at a terminal end 416 of the barrel member 408. The chamber 414 is sized to contain a volume of viscous paste (e.g., viscous dental paste), and can have the cylindrical shape as shown, defining a central axis A. The barrel member 408 can further include or carry various features that facilitate mounting of the plunger assembly 404. For example, in some embodiments, the barrel member 408 forms exterior threads 418 at the terminal end 416.

The dispensing tip 410 extends from the barrel member 408 in a direction of the longitudinal axis A, and defines a trailing end 420 and a dispensing end 422. The trailing end 420 is formed or defined at the intersection of the dispensing tip 410 and the barrel member 408. The dispensing tip 410 defines a passageway 424 that is open to the chamber 414 and is continuous to the dispensing end 402. The passageway 424 is open to an exterior of the barrel 402 at an outlet opening 426 at the dispensing end 422, and can taper in diameter from the trailing end 420 toward the outlet opening 426.

The platform 412 is formed at the dispensing end 422, and is generally configured to receive and support viscous material (not shown) dispensed (e.g., extruded) from the outlet opening 426. In some embodiments, the platform 412 can be considered as a component of the dispensing tip 410. More particularly, the platform 412 can be viewed as serving as a downstream face or surface of the dispensing tip 410, with the outlet opening 426 being formed in or defined by the platform 412.

In some embodiments, a plane P of the platform 412 is non-perpendicular relative to the central axis A. For example, the platform 412 can extend at angle $\theta$ in the range of 10°-80°, alternatively in the range of 20°-70°, alternatively in the range of 30°-60°, relative to the central axis A. As identified in FIG. 12, then, this angular relationship effectively locates a first segment 428 of the platform 412 downstream of the outlet opening 426, and a second segment 430 of the platform 412 upstream of the outlet opening 426. The downstream segment 428 can be viewed as being akin to the one or more of the platforms described above (e.g., the platform 30 of FIG. 1 is downstream of the corresponding outlet opening 56).

Returning to FIGS. 11A and 11B, the plunger assembly 404 can assume a variety of forms, and in some embodiments includes a plunger 440 and a collar 442. The plunger 440 includes or defines a shaft 444 and a handle 446. The shaft 444 terminates at a piston end 448 opposite the handle 446. Optionally, a seal member 450 is attached to or formed by the piston end 448. The shaft 444 has a threaded exterior surface 452 for coupling with the collar 442 as described below.

The collar 442 is generally configured to connect the plunger 440 with the barrel 402. In some embodiments, and as shown in FIG. 13, the collar 442 forms first and second interior threaded sections 454, 456. The first interior threaded section 454 is configured to threadably engage the exterior threads 418 (FIG. 11A) of the barrel member 408 (FIG. 11A), whereas the second interior threaded section 456 is configured to threadably engage the threaded exterior surface 452 (FIG. 11A) of the plunger shaft 444 (FIG. 11A).

Final assembly of the dispensing apparatus 400 is further reflected in FIG. 14. As shown, the collar 442 is threadably assembled to the barrel member 408, and the plunger shaft 444 is threadably assembled to the collar 442. With this construction, the piston end 448 of the plunger shaft 444 (and thus the seal member 450 carried by the piston end 448) can be advanced (and retracted) relative to the barrel member 408 by rotating the plunger 440 (e.g., user-applied rotation force at the handle 446).

FIG. 15 illustrates the supply volume 114 of the viscous paste 112 loaded into the chamber 414 in defining a viscous paste packaged article 460. The plunger 440 is manually operated to force the supply volume 114 toward the dispensing tip 410, causing a stream 462 of the viscous paste 112 to be extruded through the outlet opening 426. A user can incrementally remove portions of the extruded stream 462 as desired for a particular procedure, with the platform 412 providing a convenient, robust surface against which the extruded stream 462 can be cut.

Dispensing apparatuses, viscous paste packaged articles, and methods of use of the present disclosure provide marked improvements over previous designs. Viscous dental pastes, and other highly viscous materials, are presented to dentists (or other end user) in a packaging format that safely contains the viscous paste, and facilitates dispensing a the viscous paste in a form that is conducive to desired end use activities, for example as a single ribbon or sheet. In this regard, the platform supports the extruded ribbon in an unobstructed manner such that the user can easily access and retrieve small portions of the extruded viscous paste. Waste and possible cross-contamination concerns are greatly minimized.

Although the present disclosure has been described with reference to preferred embodiments, workers skilled in the art will recognize that changes can be made in form and detail without departing from the spirit and scope of the present disclosure.

What is claimed is:

1. An apparatus for dispensing a viscous dental paste, the apparatus comprising:
a barrel member defining a chamber for maintaining a volume of a viscous paste;
a dispensing tip extending from the barrel member and defining a passageway open to the chamber, the dispensing tip terminating at a dispensing end opposite the barrel member, the dispensing end forming an outlet opening, wherein the outlet opening is open to the passageway and is circumscribed by a continuous wall defining an interior surface and an exterior surface; and
a platform projecting from the dispensing end and defining opposing, first and second major faces, wherein the first major face is arranged to receive paste dispensed through the outlet opening, and the second major face is contiguous with a section of the exterior surface;
wherein viscous paste can be dispensed from the chamber directly onto the platform via the dispensing tip.

2. The apparatus of claim 1, further comprising a plunger including a plunger end slidably disposed within the chamber.

3. The apparatus of claim 1, wherein the first major face is contiguous with a section of the interior surface.

4. The apparatus of claim 1, wherein the second major face is a continuation of the exterior surface.

5. The apparatus of claim 1, wherein a perimeter shape of the outlet opening is elongated and defines opposing, first and second sides and opposing, first and second ends, a dimension of each of the sides being greater than a dimension of each of the ends, and further wherein the platform is an extension of the second side.

6. The apparatus of claim 5, wherein a transverse dimension of the platform in a direction transverse to a direction of extension of the platform from the dispensing tip is identical to a transverse dimension of the second side.

7. The apparatus of claim 1, wherein the first major face is substantially flat.

8. The apparatus of claim 1, wherein the passageway tapers to the outlet opening.

9. The apparatus of claim 1, wherein the dispensing tip defines a trailing end at the barrel member, the dispensing tip tapering from the trailing end to the dispensing end.

10. The apparatus of claim 9, wherein relative to an upright orientation of the apparatus in which the first major face of the platform is above the second major face, the wall of the dispensing tip defines an upper segment and a lower segment, the upper segment extending downwardly toward the lower segment in extension from the trailing end to the dispensing end.

11. The apparatus of claim 1, wherein the apparatus is configured such that the outlet opening is the only opening through which material from the chamber can be dispensed from the dispensing tip.

12. A viscous paste packaged article comprising:
a dispensing apparatus including:
a barrel member defining a chamber,
a dispensing tip extending from the barrel member and defining a passageway open to the chamber, the dispensing tip terminating at a dispensing end opposite the barrel member, the dispensing end forming an outlet opening, wherein the outlet opening is open to the passageway and is circumscribed by a continuous wall defining an interior surface and an exterior surface,
a platform projecting from the dispensing end and defining opposing, first and second major faces, wherein the first major face is aligned with a section of the interior surface, and the second major face is contiguous with a section of the exterior surface; and
a volume of viscous paste contained within the chamber;
wherein the viscous paste is dispensed from the chamber onto the platform via the dispensing tip.

13. The packaged article of claim 12, wherein the viscous paste is a viscous dental paste.

14. The packaged article of claim 12, further comprising a plunger including a plunger end slidably disposed within the chamber such that a quantity of the volume of viscous paste can be dispensed onto the platform and accessible to a user by selectively advancing the plunger end within the chamber in a direction of the dispensing tip.

15. The packaged article of claim 12, wherein the system is configured such that an entirety of a quantity of the volume of viscous paste dispensed from the dispensing tip is located on the first major face of the platform.

16. The packaged article of claim 12, wherein the first major face is contiguous with a section of the interior surface.

17. The packaged article of claim 12, wherein the passageway tapers to the outlet opening.

18. The packaged article of claim 12, wherein the apparatus is configured such that the outlet opening is the only opening through which the viscous paste in the chamber can be dispensed from the dispensing tip.

19. A method of applying viscous dental paste to a patient, the method comprising:
- receiving a dispensing apparatus loaded with a volume of viscous dental paste, the apparatus including:
- a barrel member defining a chamber within which the viscous dental paste is contained,
- a dispensing tip extending from the barrel member and defining a passageway open to the chamber, the dispensing tip terminating at a dispensing end opposite the barrel member, the dispensing end forming an outlet opening, wherein the outlet opening is open to the passageway and is circumscribed by a continuous wall defining an interior surface and an exterior surface,
- a platform projecting from the dispensing end and defining opposing, first and second major faces, wherein the first major face is arranged to receive viscous dental paste dispensed through the outlet opening, and the second major face is contiguous with a section of the exterior surface;
- operating the apparatus to force the volume of viscous dental paste toward the dispensing tip;
- wherein in response to the step of operating the apparatus, a quantity of the volume of viscous dental paste is dispensed onto the first major face of the platform;
- removing a portion of the quantity of viscous dental paste from the platform; and
- applying the portion to the patient.

20. The method of claim 19, wherein the step of operating the apparatus includes dispensing a single ribbon of viscous dental paste from the dispensing tip.

\* \* \* \* \*